(12) United States Patent
Chen et al.

(10) Patent No.: US 8,097,028 B2
(45) Date of Patent: Jan. 17, 2012

(54) PHOTOREACTIVE SYSTEM AND METHODS FOR PROPHYLACTIC TREATMENT OF ATHEROSCLEROSIS

(75) Inventors: James C. Chen, Bellevue, WA (US); Nicholas Yeo, Great Bookham (GB); Phillip Burwell, Snohomish, WA (US); Thomas Wenger, Durham, NC (US)

(73) Assignee: Light Sciences Oncology, Inc., Bellevue, WA (US)

( * ) Notice: Subject to any disclaimer, the term of this patent is extended or adjusted under 35 U.S.C. 154(b) by 1346 days.

(21) Appl. No.: 11/357,358

(22) Filed: Feb. 17, 2006

(65) Prior Publication Data

US 2007/0038204 A1    Feb. 15, 2007

Related U.S. Application Data

(60) Provisional application No. 60/654,576, filed on Feb. 17, 2005.

(51) Int. Cl.
*A61N 5/06* (2006.01)
(52) U.S. Cl. ............... 607/88; 606/7; 606/10; 128/898
(58) Field of Classification Search .......... 606/3, 7, 606/10–16; 607/88–92; 128/898
See application file for complete search history.

(56) References Cited

U.S. PATENT DOCUMENTS

| 4,773,899 A | 9/1988 | Spears ............ 604/20 |
| 4,790,315 A | 12/1988 | Mueller, Jr. et al. .......... 128/344 |
| 4,799,479 A | 1/1989 | Spears ............ 128/303.1 |
| 5,370,608 A | 12/1994 | Sahota et al. ............ 604/20 |
| 5,417,653 A | 5/1995 | Sahota et al. ............ 604/20 |
| 5,445,608 A * | 8/1995 | Chen et al. ............ 604/20 |
| 5,709,653 A * | 1/1998 | Leone ............ 604/20 |
| 6,086,558 A | 7/2000 | Bower et al. ............ 604/96 |
| 6,445,011 B1 | 9/2002 | Hirano et al. ............ 257/99 |
| 6,661,167 B2 | 12/2003 | Eliashevich et al. .......... 313/512 |
| 6,749,623 B1 | 6/2004 | Hsi et al. ............ 607/88 |
| 6,784,460 B2 | 8/2004 | Ng et al. ............ 257/95 |

(Continued)

FOREIGN PATENT DOCUMENTS

WO    03/094695    11/2003

(Continued)

OTHER PUBLICATIONS

U.S. Appl. No. 11/323,319, filed Dec. 30, 2005, Burwell et al.

(Continued)

*Primary Examiner* — Ahmed Farah
(74) *Attorney, Agent, or Firm* — Seed IP Law Group PLLC (57) ABSTRACT

The present invention provides a prophylactic light activated treatment method for subjects at risk of a plaque-mediated thrombotic event, such as acute coronary syndromes. In one embodiment, the subject receives a dose of photosensitizer sufficient to result in a concentration of photosensitizer in the neovascularization associated with atherosclerotic disease to permit effective photodynamic therapy. Light of a wavelength that excites the photosensitizer, but that does not to any significant extent penetrate to an adventitial layer of the blood vessel, is applied to the region of the blood vessel. The therapeutic light dose, which may be applied in sequential stages, is sufficient to cause closure of neovasculature leakage and lead to plaque stabilization and reduced adverse clinical outcomes. The present invention further provides light transmission devices and systems useful in carrying out the methods of the present invention.

20 Claims, 6 Drawing Sheets

U.S. PATENT DOCUMENTS

| | | | |
|---|---|---|---|
| 6,800,086 B2 | 10/2004 | Strong | 607/88 |
| 6,958,498 B2 | 10/2005 | Shelton et al. | 257/99 |
| 7,015,516 B2 | 3/2006 | Eliashevich et al. | 257/103 |
| 7,107,997 B1 * | 9/2006 | Moses et al. | 128/898 |
| 7,396,354 B2 * | 7/2008 | Rychnovsky et al. | 606/15 |
| 2001/0037080 A1 | 11/2001 | Mueller et al. | 604/20 |
| 2002/0183301 A1 | 12/2002 | Rychnovsky | 514/185 |
| 2003/0055307 A1 | 3/2003 | Elmaleh et al. | 600/1 |
| 2003/0097122 A1 | 5/2003 | Ganz et al. | |
| 2003/0103995 A1 | 6/2003 | Hamblin et al. | 424/185.1 |
| 2004/0208855 A1 | 10/2004 | Allison et al. | 424/93.7 |
| 2005/0228260 A1 | 10/2005 | Burwell et al. | 600/408 |

FOREIGN PATENT DOCUMENTS

| | | |
|---|---|---|
| WO | 2006/031934 A2 | 3/2006 |

OTHER PUBLICATIONS

U.S. Appl. No. 60/640,382, filed Dec. 30, 2004, Burwell et al.

Hasan, T., et al., "Detection and Therapy of Vulnerable Plaque with Photodynamic Compounds," 1985, accessed Feb. 16, 2006, URL=http://www.partners.org/techtransfer/availabletechnologies/viewprinter.asp?id=130762, 3 pages.

Allison et al., "Photosensitizers in clinical PDT," *Photodiagnosis and Photodynamic Therapy*, 1:27-42, 2004.

\* cited by examiner

PHOTOREACTIVE SYSTEM AND METHODS FOR PROPHYLACTIC TREATMENT OF ATHEROSCLEROSIS

BACKGROUND OF THE INVENTION

1. Field of the Invention

The present invention relates to the treatment and prevention of atherosclerosis and other proliferative diseases associated with neovascularization within the cardiovascular system. In particular, the present invention provides methods and systems for using photodynamic therapy to modify the atherosclerotic disease process.

2. Description of the Related Art

Cardiovascular disease (CVD) is a major health problem throughout the world. In the United States alone, roughly 2600 people die each day as a result of cardiovascular disease. CVD includes dysfunctional conditions of the heart, arteries, and veins that supply oxygen to vital life-sustaining areas of the body like the brain, the heart itself, and other vital organs. Two prominent forms of cardiovascular disease are cardiovascular obstructive disease and acute coronary syndrome.

Cardiovascular obstructive disease, also referred to as ischemic heart disease or stenosis, results from obstruction of blood flow to the heart. In general, this results because excess fat or plaque deposits are narrowing the blood vessels that supply oxygenated blood to the heart. Excess buildup of fat or plaque are respectively termed arteriosclerosis and atherosclerosis. These blockages usually result in oxygen-starvation of heart muscle tissue and subsequent injury to the tissue, which is, in most cases, irreversible and may prove fatal. Equally significant is inadequate oxygen flow to the brain, which may cause a stroke.

In recent years, a great deal of research has been devoted to the treatment of vascular obstructive disease, and treatment methods such as balloon angioplasty have become standard treatment for stenosis. In this procedure, once the location of stenosis has been identified by any of a variety of known techniques, an angioplasty catheter is inserted into the blocked vessel using a guidewire. A balloon on the catheter is inflated at the blockage site to push open the blocked vessel.

Unfortunately, however, in many cases, vessels recoil to original narrowed lumen or re-stenose (became re-blocked with plaque and/or scar tissue resulting from injury caused by distension of the vessel by the balloon) within a short period of time. Attempts to prevent recoil and/or restenosis include the use of stent devices that are permanently implanted within the vessel to hold it open at the site of the angioplasty and thereby prevent elastic recoil of the vessel following angioplasty. While this is successful in preventing recoil, it was found that the stent itself provided a stimulus for restenosis. As a result, new stents were created that have coatings to reduce the body's response to the stent including those on which a drug (typically an anti-proliferative agent) was incorporated into the coating to further reduce the incidence of restenosis. These drug-eluting stents are now widely used for treatment of patients with angina, the symptomatic consequence of coronary arteries that have become significantly narrowed by atherosclerotic plaque.

Photodynamic therapy (PDT) has been explored as an alternative approach to treating cardiovascular obstructive disease and restenosis. Attempts have been made to use light treatment, e.g., PDT, as the initial treatment for blood-flow limiting vascular occlusions in patients with atherosclerotic disease. For example, U.S. Patent Publication No. 2002/0183301 describes a method in which a photosensitizer is delivered locally or systemically to a patient, and light is applied in the wavelength range 390 to 610 nm to excite the photosensitizer. The chosen wavelength is said to reduce light penetration to underlying blood vessel tissue and, thereby, reduce injury to that tissue. The PDT is said to inhibit, stabilize, or reduce occlusions in the cardiovascular system. However, because of the wavelength of light used, blood has to be removed from the region between the light and the targeted tissue, because hemoglobin in the blood might otherwise absorb the light. This publication also cautions that treatment should avoid damage to the myocardial tissue underlying the vessel, or lung tissue, and that blood intervening between the light and these tissues acts as a protective shield by absorbing the light.

U.S. Patent Publication No. 2004/0208855 describes the treatment of intimal hyperplasia or stenosis in arteriovenous fistula with PDT. In particular, this publication deals with the prevention or treatment of these conditions in grafts or fistulas created for the purpose of conducting hemodialysis. These grafts or fistulas become obstructed over time by proliferation and thrombosis. In one embodiment, a vein exterior (adventitia layer) is exposed to 690 nm wavelength light for 40 minutes; this so-called "low dose" PDT is said to be preferred to prevent massive destruction of vessel tissue. The dose provided is said to be a function of photosensitizer concentration, intensity of light irradiation, and exposure time.

The use of PDT to treat restenosis has been described, e.g., in U.S. Pat. Nos. 5,370,608 and 5,417,653. However, light treatment is not widely used, if at all, to prevent or reduce restenosis after angioplasty, with or without stenting.

Acute coronary syndrome is a subset of serious sudden-onset cardiovascular diseases, including unstable angina, acute myocardial infarction, and sudden cardiac death. Often, acute coronary syndrome occurs in patients who have no documented history of cardiovascular disease. The cardiovascular diseases associated with acute coronary syndrome are frequently caused by erosion or rupture of a specific kind of active atheromatous plaque known as a "vulnerable plaque." This plaque is also referred to referred to as a "thin-capped fibroatheroma". See, e.g., Mamoo Nakamura, et al., *Reviews in Cardiovascular Medicine*, 2004, vol. 5 Suppl. 2 (s22-33).

Figure 1:
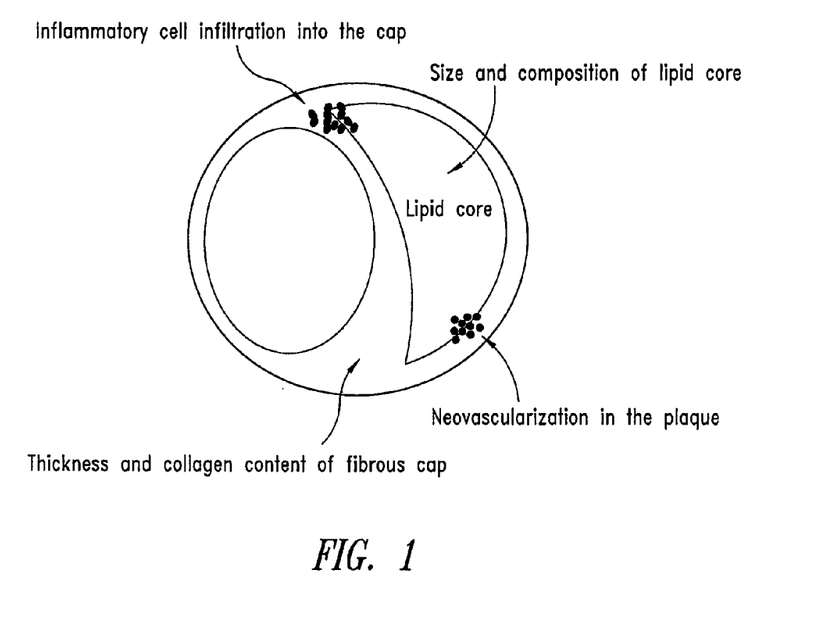
FIG. 1 is a schematic depiction of atherosclerosis, as shown in an end view cross section of a blood vessel.

A cross-section of a vein partially occluded by a vulnerable plaque is shown in FIG. 1. As depicted, the blood vessel has an open area through which blood can flow (the lumen) and is partially obstructed by a structure that has a fibrous cap and a lipid core. The lipid-rich core has been suggested to be the most powerful plaque type because it contains macrophages that produce tissue factors as well as thrombogenic lipid forms, such as lipoprotein (a). Accordingly, when this lipid core is exposed to blood (e.g., when the plaque fibrous cap erodes or ruptures), there is high risk of forming thrombus that can occlude the vessel with potential serious consequences for the subject.

In contrast to the vast majority of plaque lesions, which remain relatively stable and slowly occlude the vasculature, vulnerable plaques have higher frequency of rupture and are the leading causative agent of heart attacks, strokes, and cases of sudden death, recently estimated to be as high as 80-85%. Vulnerable plaques are structurally and functionally distinguishable from stable atherosclerotic plaques, but are almost impossible to easily detect or distinguish from quiescent or stable atherosclerotic plaques using current imaging modalities, which do not give sensitive information on plaque components and cap thicknesses (e.g., MRI, CT, myocardial perfusion imaging, angiography, intravascular ultrasound, thermography, OCT, reflectance, and spectroscopy).

Post-mortem evidence suggests that vulnerable plaque rupture occurs most frequently in areas of the coronary arteries that are less than 50% stenosed. Current therapies to ameliorate the occlusive effects of atherosclerotic plaques, such as bypass surgery and angioplasty, which focus on areas with greater than 50% stenosis, rarely remove vulnerable plaques or reduce the incidence of acute coronary syndrome. Drugs currently being developed to treat such plaques include, e.g., statins and ACE inhibitors.

However, given the significant health problems associated with acute coronary syndromes, and in light of the recent advancements in detecting the presence of underlying vulnerable plaques, there is clearly an immediate need for improved methods and devices for treating acute coronary syndromes, including, e.g., methods and devices to prevent the growth and rupture of vulnerable plaques through PDT.

BRIEF SUMMARY OF THE INVENTION

The present invention provides methods of treating subjects at risk of acute coronary syndromes (unstable angina, acute myocardial infarction and sudden cardiac death), including but not limited to those resulting from atherosclerotic disease of the coronary arteries. In one embodiment, the methods are prophylactic methods. The invention also provides novel systems useful in carrying out the methods of the present invention.

Prophylactic treatment of one of more of the epicardial coronary arteries in patients with atherosclerotic disease in accordance with the present invention beneficially modifies the atherosclerosis through closure of leakage from neovessels associated with the atherosclerotic plaque and reduces the incidence of plaque erosion or rupture that causes acute coronary syndromes. Accordingly, the invention also provides methods of treating atherosclerotic and other proliferative disease associated with neovascularization at other locations within the cardiovascular system (e.g., carotid artery disease, peripheral artery disease in the vasculature of the legs, arteriovenous graft dysfunction in patients undergoing dialysis or vein graft disease in patients receiving coronary bypass graft surgery). In certain embodiments, the methods of treatment provided by this invention are of short duration, and can be carried out under standard percutaneous interventional conditions suitable for well-known procedures such as angioplasty.

In one embodiment, the present invention provides a method of treating or preventing an acute coronary syndrome that includes identifying and selecting a subject with atherosclerotic disease of one or more of the coronary arteries or who may be at risk of acute coronary syndromes. The identification of risk could be made based on clinical history, risk-factor assessment or on non-invasive or invasive diagnostic tests, including, e.g., imaging. In the treatment provided by this invention, the subject receives through systemic intravenous or direct intravascular injection into the diseased vessel, a dose of photosensitizer sufficient to result in a concentration of photosensitizer in the neovascularization associated with the atherosclerotic plaque that permits effective light activated therapy. In certain embodiments, before commencing light activation of the distributed photosensitizer, the artery being treated is flushed with a biocompatible translucent liquid, such as saline, that transiently displaces the blood from the vessel to be treated, together with the photosensitizer therein contained in the blood. The flushing process may be facilitated, for example, by balloon occlusion at a proximal site in the vessel to be treated and by introducing the flushing medium at a point distal to the balloon occlusion. The method proceeds with irradiating the internal surface of the vessel with light of a wavelength that excites the photosensitizer in the neovascular target but which does not to any significant extent penetrate to the vasa vasorum that exists in the outside adventitial layer of the blood vessel. After a period of irradiation, the method permits reperfusion of the flushed portion of the blood vessel with blood through removal or disabling of the occluding device (e.g., balloon deflation). Then, steps of flushing, occlusion and irradiation may be repeated in one or more cycles until a sufficient (therapeutic) light dose has been administered to treat a desired region of or the entire segment of the atherosclerotic diseased vessel. Light so administered activates the photosensitizer, causing a biological effect that seals the neovasculature associated with the atherosclerotic plaque, thus preventing the entry of blood and inflammatory cells into the plaque. The outcome of treatment provided by this invention is reduced plaque expansion and increased plaque stability.

In another embodiment, the present invention provides a system useful for practicing a method of the present invention. In one embodiment, the system includes a catheter sized for insertion into blood vessels to be treated with light activated treatment. The catheter includes an inflatable proximal occlusion balloon and is equipped with a multi-channel lumen to enable catheter delivery into the diseased vessel over a standard guidewire and for other intervention utilities including inflation of the balloon, flushing and delivery of the light-generating module. In one embodiment, the system also includes a photosensitizer having peak energy absorption in the violet-blue sector of visible light ranging from about 410 nm to about 475 nm. The system includes an endovascular light-generating module chosen for its output wavelength to match the excitation wavelength of the photosensitizer. Violet-blue light is also preferred for light activation since the high level of scattering in the vessel wall will maximize homogeneity of the delivered light dose within the treatment target and accommodate the well-known multi-focal distribution of atherosclerotic disease. The light-generating module is sized for insertion into the lumen of the catheter to deliver light to the vessel wall at the required energy dose for therapeutic activation of the photosensitizer. Further, in various embodiments, the system includes such ancillaries as may be necessary or desirable in the interventional suite or such other location as the treatment may be performed.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility.

FIGS. 4-7 are schematic diagrams of light emitters that are useful to provide light to treat plaque within blood vessels, in accordance with the invention. The light emitter of FIG. 4 includes a conical reflector; the light emitter of FIG. 5 includes a soft; atraumatic tip; and light emitter of FIG. 6 includes a Ring of Die.

FIG. 7 is a schematic diagram depicting a 0.014 guidewire surrounded by 0.25 mm die in an approximately 1.1 mm diameter (<4F) profile.

DETAILED DESCRIPTION OF THE INVENTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with light emitters, light emitting diodes, lasers, catheters, guide wires, and controllers have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Further more, the particular features, structures, or characteristics may be combined in any suitable manner in one or more embodiments.

The present invention is based, in large part, on the discovery of a novel method of reducing or preventing neovascular leakage, including neovascular leakage and rupture of atherosclerotic plaques, including, e.g., vulnerable plaques. Accordingly, in one embodiment, the present invention provides methods, apparatus, and systems related to light activated treatment (i.e., PDT) that reduces or prevents neovascular leakage from and rupture of atherosclerotic plaques and, thus, prevents acute coronary syndromes, including, but not limited to, unstable angina, acute myocardial infarction, and sudden cardiac death.

Recently, advancements have been made in the detection of vulnerable plaques, including the use of photosensitizers. See, e.g., U.S. Patent Application Publication No. 20030103995. According to one method being developed, PDT photosensitizer, fluorescent, or photoactive compounds are targeted for binding to shoulder macrophages, lymphocytes, or smooth muscle cells in vulnerable plaque, preferably coupled to ligands that bind to surface scavenger receptors. Alternatively, the PDT compositions are targeted to increased lipid populations in the plaque core or proteases found in the fibrous cap. Multiple PDT compounds (chlorin-e6 conjugates) have been used to selectively detect lesions in rabbit model systems analogous to vulnerable plaque in humans. According to one method, photoactivation is carried out using a specifically designed intravascular device that delivers excitation light to the plaque surface inside the artery and receives emitted fluorescence signals which are transmitted to an analysis instrument.

In another method, radionuclide (beta or gamma emitters) or paramagnetic contrast imaging agents are coupled to macromolecular targeting carriers and/or the PDT compounds that localize to the vulnerable or actively forming plaque components. The labeled imaging agents are small molecules that rapidly (less than 6 hours) localize, selectively and irreversibly, to the sites of the lesion. The imaging agents can be administered alone or in conjunction with the PDT compounds. Both beta and gamma radionuclide detection probes (18F-FDG, 99mTc-fMet-Leu-Phe, 99mTc-Ap4A) have been used successfully by the to selectively detect lesions in rabbit model systems analogous to vulnerable plaque in humans.

It has also been proposed that these PDT or nuclear agents may be used to prevent plaque rupture, either by stabilizing the structure of existing components or specifically eliminating the destabilizing populations of inflammatory cells, lipids, or proteases. In addition, the use of PDT compounds to treat vulnerable or actively forming plaque, has been described, including the use of PDT agents to cross-link extracellular matrix proteins, thereby stabilizing the fibrous cap against rupture through activation of the same dye used for detection or administration of a second species. It is believed that additional targeting of PDT photosensitizer compositions to shoulder macrophages, lymphocytes or other inflammatory cells allows for selective destruction through light activation and apoptosis. Controlled application of PDT allows cells to undergo only apoptosis rather than induction of necrotic cellular responses thereby reducing inflammatory responses in the high risk area. Death of these cells leads to improved stability of the region through a reduction in the release of proteases or other factors that inhibit extracellular matrix production as well as an overall decrease local secretion prothrombogenic factors. This technology has been successfully demonstrated in the rabbit plaque model system for the targeted destruction of plaque macrophages using clorin-e6 conjugates and commercial lasers.

Diagnostic probe/catheter devices designs that deliver excitation light to the plaque surface and receive emitted fluorescence signals that are transmitted to an analysis instrument have also been described. If an appropriate diagnostic signal is detected, the same device delivers light therapy to eliminate specific targeted components. The light for diagnosis and treatment is delivered via a laser or optical fiber that is combined with an appropriate intravascular catheter. Alternatively, for open surgical sites, the light sources considered appropriate include broadband conventional light sources, broad arrays of LEDs, and defocused laser beams.

According to the present invention, pathological neovascularization within the wall of a blood vessel affected by atherosclerotic disease is a therapeutic target for intervention with light activated treatment. Without being bound by any particular theory, it is understood that halting the leakage of blood and/or inflammatory cells from neovessels present in and around the site of atherosclerosis contributes to reducing the morbidity and mortality of acute coronary syndromes that may otherwise occur if the atherosclerotic plaque leaks, erodes, or ruptures. In various embodiments, the methods, apparatus, and systems of the present invention prevent or reduce plaque neovascular leakage on a regional basis within a vessel or pan-regionally within more than one vessel. The treatment can be provided either on its own or as part of an acute-plus-chronic treatment strategy (e.g., light activated treatment with follow-on pharmacotherapy), for patients at risk of developing acute coronary syndromes.

Figure 2:
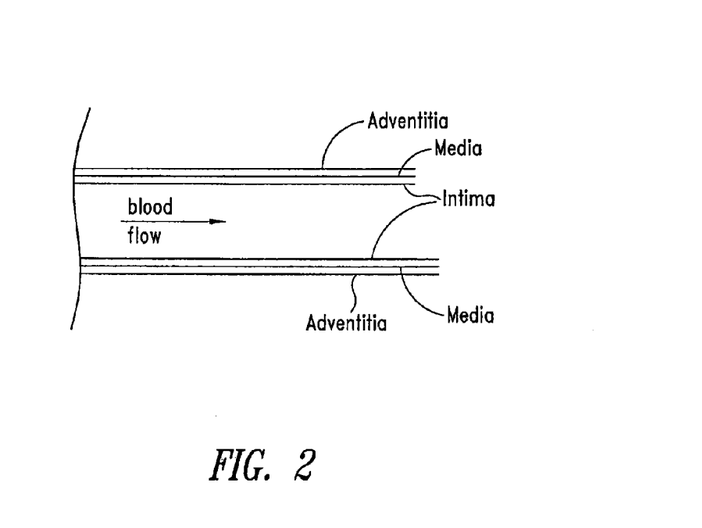
FIG. 2 is a longitudinal cross sectional view of a typical blood vessel showing layers of the vessel wall.

To better appreciate aspects of the invention, it should be noted that a typical cardiovascular blood vessel has a wall that has three layers: an outer layer known as the adventitia (300-400 microns thick) that has a blood supply (the vasa vasorum); an inner layer known as the intima (100-150 microns thick); and a layer between these known as the media. This is schematically illustrated in FIG. 2, a longitudinal cross section through a blood vessel.

The development of coronary atherosclerosis is a complex biological process characterized by the formation of a continuum of lesions that range from biologically inactive, but hemodynamically significant (i.e., obstructive to blood flow) at one end of the spectrum to biologically active, and hemodynamically insignificant (i.e., not obstructive to blood flow), at the other end. As discussed above, some biologically active lesions are commonly referred to as "vulnerable plaques." These are characterized by a thin fibrous cap, large lipid-core (often necrotic) with a high density of macrophages, as shown in FIG. 1. There is also, significantly, neovasculature extending from the vasa vasorum of the adventitial layer, which develops in response to the angiogenic stimulus caused by hypoxia resulting from the developing atherosclerotic plaque, which thickens the intima. The vasa vasorum contributes to the instability of the plaque through plaque expansion and inflammation. Upon erosion or rupture, these plaques may cause clotting that may close the vessel completely, resulting in an acute coronary syndrome.

According to the present invention, treatments that reduce plaque vulnerability to erosion or rupture mitigate the acute risk of potentially fatal coronary thrombosis. Certain embodiments of the invention are, therefore, directed to the prophylactic treatment of atherosclerosis using light activated therapy to reduce the risk of rupture. In particular, the invention recognizes a relationship between plaque vulnerability to erosion or rupture and underlying neovascularization that develops due to the angiogenic stimulus caused as the atherosclerotic plaque develops within the artery wall.

Some atherosclerotic lesions are associated with positive remodeling of the vessel wall in which the wall of the vessel accommodates the accumulating plaque without necessarily restricting blood flow. Culprit lesions that lead to acute coronary ischemic syndromes are typically not significantly stenotic before rupture. For example, according to Schoenhagen, P., et al., *Am. J. Cardiol.*, 89:1354-1359, 2002, as many as 70% of patients diagnosed with myocardial infarction have less than 50% coronary stenosis at the location of the thrombotic event. Thus, these lesions may be asymptomatic at the time of myocardial infarction. This contrasts with other plaque deposits that may grow into the lumen of the vessel, progressively occluding blood flow and causing myocardial ischemia, which is commonly associated with angina, particularly on exertion. Accordingly, it should be understood that within the overall disease process, a mixture of lesion types are possible.

Atherosclerotic plaques, shown in FIG. 1, that become susceptible to erosion and/or rupture and are treated according to the present invention may have a number of characteristics, including one or more of those described below.

In many plaques, a lipid-rich core (originating from death of lipid-laden macrophages or foam cells and from accumulation of lipids in the extracellular matrix) is present in the central portion of an eccentrically thickened intima. The shoulder region of the fibrous cap over the lipid-rich core is commonly populated with macrophages and macrophage derived foam cells. Plaques prone to rupture have a thinner fibrous cap at the shoulder, increased inflammatory cells, and a relative paucity of smooth muscle cells.

Atherosclerotic plaques may have a large necrotic core with an overlying thin fibrous cap (<65 microns) infiltrated by macrophages. Such plaques have been described as thin-capped fibroatheroma (TCFA; Virmani, R. et al., *J. Interv. Cardiol.*, 16:267-272, 2003). Importantly, over 50% of TCFAs are located in the proximal portions of the coronary tree, and over 40% are found in the left anterior descending artery (LAD). Only 30% are located in the same artery as the culprit lesion, pointing to the multi-focal development of vulnerability to acute coronary syndromes.

Monocytes, macrophages and T-lymphocytes are the predominant inflammatory cells present at the site of superficial erosion of an atherosclerotic plaque or rupture. Matrix-metalloproteinases produced by macrophages may contribute to plaque disruption through increased degradation of collagen and other extracellular matrix components in the fibrous cap.

Normal coronary arteries benefit from an organized network of small blood vessels within the adventitia, the vessel's outermost layer. This network, known as the vasa vasorum, supplies oxygen and nutrients to the muscular sheath of the vessel that is too far distant from the lumen of the vessel to receive these necessities by normal diffusion. In the atherosclerotic vessel, plaque deposition in the intima exacerbates the oxygen debt (hypoxia) in the vessel wall, triggering downstream angiogenic factors, such as vascular endothelial growth factors, that lead to the formation of new blood vessels (angiogenesis) in the affected region. As the atherosclerotic process continues, a proliferation of neovessels buds off the adventitial vasa vasorum and grows through the media into the thickened intima at the site of the atherosclerotic plaque.

It was previously postulated that neovascularization may also grow from the arterial lumen itself outwards towards the plaque, in addition to the neovascularization developing from the adventitia. However, it appears from the latest research that such luminal neovascularization in the human coronary artery (and perhaps in other arteries generally) does not occur, or, if it does occur, then at the site of an atherosclerotic plaque, any luminal neovascularization is likely to be disrupted and dysfunctional.

Thus, without being bound to any particular theory, it is understood according to the present invention that neovascularization causes plaque instability. Neointimal capillaries exist at the base and shoulders of thin-capped fibroatheroma (vulnerable plaque). Neovascularization is proteolytic, thereby causing degradation of the collagen and fibrin matrix, and thereby destabilizing plaques. Neovascularization is enhanced by and promotes inflammatory cell recruitment (pathological positive feedback). Plaque neovessels cause microhemorrhages into the plaque that increase inflammation and other destabilizing processes.

In addition, it is further understood that neovascularization causes plaque progression. Neovessel density in plaques correlates with inflammatory cell density and atherosclerotic lesion progression. As atherosclerosis progresses, neovessel endothelium predominates over artery lumen endothelium. Plaque neovessels are a source for macrophages, inflammatory mediators, and growth factors, and a source of cholesterol via re blood cell membranes from micro-hemorrhages. There is an association among intra-plaque hemorrhage, increase in the size of the necrotic core, and lesion instability in the plaque. Intra-plaque hemorrhage from neovascularization represents a critical event in the induction of instability in vulnerable lesions.

It is theorized therefore, that neovascularization is the underlying mediator of the biological processes that result in plaque rupture. Further, the evolution of neovascularization at the base and shoulders of the atherosclerotic plaque provides significant contribution to the transition from stable plaque to unstable plaque. Therefore, according to the present invention, treatment that results in closure of or a reduction of the neovascularization in plaque leads to beneficial outcomes that individually or collectively mitigate the risk of plaque rupture, thrombosis, and acute ischemic events, both in the coronary and other vascular settings where plaque neovascularization occurs, such as in the carotid.

These beneficial outcomes include a reduction in intraplaque hemorrhage, reduced inflammatory cell infiltration into plaques, and reduced angiogenic stimulus. Reduction in intraplaque hemorrhage from fragile neovessels reduces the extravasation of platelets and erythrocytes leading to a reduction in the deposition of free cholesterol, foam cell formation and ceroid production, and stabilization in the size of necrotic core and plaque volume. Reduced inflammatory cell infiltration into plaque by down-regulated expression of leukocyte adhesion molecules leads to a reduction in macrophage generated matrix metalloproteinases and, in turn, lessen the destruction of collagen and other extracellular matrix components important to the structural integrity of the fibrin cap covering the plaque. Reduced angiogenic stimulus (due to reduced inflammation at site of plaque) slows the formation of any further neovascularization, thus providing a therapeutic bridge while the disease modifying effect of systemic therapy (cholesterol lowering, anti-thrombotic, anti-angiogenic) achieves a therapeutic level.

In their various embodiments, each of the methods, apparatus, devices and systems of the present invention provide one or more of the foregoing benefits.

Methods of Treating and Preventing Atherosclerotic Disease and Acute Coronary Syndromes In various embodiments, the present invention provides methods of treating and preventing cardiovascular disease, including atherosclerosis, e.g., stenosis and restenosis, as well as acute cardiac syndromes, including, but not limited to unstable angina, acute myocardial infarction, and sudden cardiac death. These methods generally comprise photodynamic therapy (PDT) of at least a region of a blood vessel having an atherosclerotic plaque, e.g., wherein said plaque has neovasculature. It is further understood that the methods and devices described herein may also be used to treat other diseases of the cardiovascular system associated with neovascularization, including, but not limited to, carotid artery disease, peripheral artery disease, e.g., in the vasculature of the legs, arteriovenous graft dysfunction, and vein graft disease.

PDT is a process whereby light of a specific wavelength or waveband is directed toward target cells, tissues, or biological structures that have been rendered photosensitive through the administration of a photo-reactive, photo-initiating, or photosensitizing agent. This photo-reactive agent has a characteristic light absorption waveband and is commonly administered to a subject via intravenous injection, oral administration, or by local delivery to the treatment site. In the context of the treatment of atherosclerosis, once the photo-reactive agent has distributed to the neovascularization in and around the target plaque, the atherosclerosis can then be treated by exposing the neovascularization to light of an appropriate wavelength or waveband that substantially corresponds to the absorption wavelength or waveband of the photo-reactive agent. The wavelength of light delivered to the neovascularization treated with the photo-reactive agent causes the agent to undergo a photochemical reaction with oxygen in the localized targeted cells, to yield free radical species (such as singlet oxygen), which cause localized cell lysis or necrosis. This results in stabilization of the plaque.

Methods of the present invention may be practiced in a localized region of a vessel, or, alternatively, entire vessels or regions thereof may be treated, e.g., prophylactically. Subjects treated according to the methods of the present invention may be diagnosed with atherosclerotic disease or, alternatively, they may be considered at risk of atherosclerotic disease. Thus, methods of the present invention include treatment of pre-existing atherosclerotic disease, as well as prophylactic treatment to prevent atherosclerotic disease or an acute coronary syndrome or event. In particular embodiments, a subject is a mammal, and in one embodiment, a subject is a human.

In one embodiment, a method of the present invention generally includes delivering an appropriate dose of a photosensitizer to the subject, and generating light inside the diseased (or suspected as diseased) vessel once the photosensitizer has distributed to the neovascularization in and around the target plaque. In a particular embodiment, light is administered to an interior surface of a blood vessel. In particular embodiments, the photosensitizer is administered systemically, e.g., intravenously or intraarterially. In other embodiments, the photosensitizer is administered locally to a vessel or region thereof to be treated.

In specific embodiments, the region of the vessel to be treated is flushed with a substance, e.g., with saline, prior to generating light inside the vessel and, thus, activating the photosensitizer. The flush excludes light-absorbing blood from the region, thereby permitting use of a light source that illuminates the vessel wall with a wavelength of light that (1) excites the photosensitizer, (2) does not penetrate to any significant extent into the adventitia of the vessel, and (3) does not cause damage to normal arterial endothelium within the region of treatment. Accordingly, in one embodiment, the photosensitizer is administered in the substance used to flush the treated vessel or region thereof. Accordingly, in particular embodiments, the substance used for flushing comprises a photosensitizer. It is understood that the photosensitizer may, therefore, be administered prior to or during flushing. In addition, an additional flushing may be performed after administration of flushing substance comprising photosensitizer, e.g., with a substance such as saline lacking photosensitizer, in order to remove excess photosensitizer.

Depending on the extent of the disease in the vessel, or in the case that an entire artery in the heart is being treated prophylactically, particular embodiments of the methods of the present invention accommodate a need to regularly perfuse the downstream tissues supplied by the vessel, by comprising cyclical reperfusion of blood through the treated artery, followed by further saline flushes, until the entire targeted region has received the prescribed light activation dose. Thus, in one embodiment, the application of light to activate the photosensitizer is regionally fractionated with blood reperfusion intervals to enable a length of vessel to be treated without occluding flow for the entire treatment process. Since blood flow in plaque neovascularization predominantly originates from the adventitial vasa vasorum, which is the normal vascular network supplying the outer and middle layers of the artery, blood and photosensitizer resident in the neovascular bed underlying the plaque are not disturbed by flushing the artery affected by atherosclerosis.

In other embodiments, including those wherein a light emitter is juxtaposed directly against the vessel wall being treated, there is no need to flush the blood from the vessel prior to the administration of light.

In accordance with the present invention, the photosensitizer must be excited by light of a wavelength that secures good photonic energy distribution in the intima containing the atherosclerosis (or suspected of containing it) but which is substantially attenuated before penetrating into the adventitia, since vasavasorum closure in the adventitia is undesirable. Thus, the activating wavelength and optical power are chosen such that the lights irradiance, as it transmits across the media, is attenuated substantially below the threshold at which the generation of singlet oxygen creates irreversible damage. This dictates a wavelength parameter that can be used to select an appropriate photosensitizer. In one embodiment, the light used for activation of the photosensitizer is coherent or non-coherent light.

Furthermore, in the coronary arterial setting, oxyhemoglobin in the blood within the artery and within the artery's vasa vasorum and any neovascularization that may have developed from it will strongly absorb light. Whole blood exhibits two strong absorption bands at 540 nm and 577 nm and two other absorption peaks at 415 nm and 940 nm, predominately due to the high concentration of oxyhemoglobin chromophore in arterial blood. At 415 nm, the penetration depth, defined as the distance at which the energy incident on the tissue surface is extinguished by 37% (1/e), is approximately 100-150 microns. Thus, light at this wavelength is considered particularly useful for containing the effects of PDT within the intima and media of the atherosclerotic arterial wall. This may also be of importance from a safe treatment perspective, since the light will be further and rapidly attenuated by oxyhemoglobin in blood in the adventitial vasa vasorum and thus stands to mitigate treatment damage to surrounding normal tissue.

In certain embodiments of the present invention, the light wavelength is in the range of from about 410 to about 475 nm. In one embodiment, the light wavelength is in the range of 410 to 475 nm. Thus, photosensitizers having an excitation wavelength within this range are suitable for use. Photosensitizers excited by light in this wavelength range are preferred because violet-blue light is highly scattered and energy is rapidly attenuated during transmission. This invention therefore provides a basis on which unwanted activation of the photosensitizer in the adventitial vasa vasorum can be minimized or even mitigated completely. Thus when violet-blue light is generated within the lumen of the vessel being treated it provides strong activation of the photosensitizer in plaque neovascularization but is attenuated before reaching the adventitial layer of the vessel in which the normal vasa vasorum is located. In particular embodiments of the invention, the photosensitizer is mono-N-aspartyl chlorin e6 (Talaporfin Sodium), which is strongly excited by light having a wavelength in the 410-415 nm range.

Other photosensitizers having excitation wavelengths within the specified range may also be used, as long as they also meet other criteria set forth herein. Useful photosensitizers may be selected, using the criteria set forth herein, from those listed in U.S. Pat. No. 6,800,086, columns 6-20, which is fully incorporated herein by reference.

In one embodiment, methods of the present invention utilize photosensitizers that, upon delivery, rapidly distribute to the vessels to be treated to minimize intervention time. Nonetheless, other photosensitizers that are not so readily dispersed within the vessel tissue are also useful. The PDT compositions (e.g., photosensitizers) can be standard dyes known in the art or derivatives made through linkage to macromolecular targeting carriers (e.g., growth factors, microspheres, liposomes, peptides, antibodies, or lipoproteins).

When the photosensitizer in use is Talaporfin Sodium, drug dose may vary with the particular subject, but it is generally within the range from about 0.1 to about 2.0 mg/kg of body weight. In certain embodiments, the drug dose is in the range of 0.1 to about 1.0 mg/kg. In another embodiment, the drug dose is in the range of about 0.5 mg/kg or less. It is understood that the dose will vary depending upon many factors, and therefore the dose is not generally limited by any considerations other than that it should be sufficiently high to ensure that a therapeutic amount is present in tissue to be treated to carry out an effective PDT. Such dosages can be readily determined by one skilled in the art.

In various embodiments, the light source is a laser light source, or a non-laser light source, or a coherent light source, or a non-coherent light source, as long as the wavelength of light emitted meets the criteria set forth herein, and it has sufficient energy to supply an effective light dose to carry out the PDT procedure within the period of time for the procedure.

In another embodiment, the invention provides prophylactic treatment for subjects at risk of an adverse coronary event resulting from coronary artery disease. In this case the term "prophylactic" should be broadly understood to encompass treatments carried out on subjects that are (a) asymptomatic (for example, subjects with substantially elevated risk-factors for acute coronary syndromes but without angina); or (b) have confirmed diagnosis of coronary atherosclerosis either through symptomatic evidence of blood-flow obstruction (e.g., angina) and/or by non-invasive investigation (for example, raised C Reactive Protein, magnetic resonance (MR) or multi-slice computed-tomography (CT) imaging) and/or by invasive detection (e.g., by angiography, intravascular ultrasound (IVUS), optical coherence tomography (OCT), or other techniques).

In one embodiment, methods of the present invention are practiced without precise knowledge of the location of atherosclerosis within any blood vessel. This embodiment of the invention represents a significant advantage in that it eliminates the need for invasive diagnostic procedures to carry out atherosclerotic plaque mapping and assessment of individual sites of plaque as to vulnerability to erosion or rupture. Instead, according to the present invention, the vessels suspected of being diseased through atherosclerosis are treated in their entirety, if desired. The areas that are in fact not diseased are substantially unaffected by the treatment, while the affected areas in which pathologic neovascularization is present are effectively treated.

Accordingly, the invention provides a method of treating or preventing an adverse coronary event or syndrome, comprising administering an appropriate dose of a photosensitizer to a subject at risk of an adverse coronary event or syndrome, flushing a region of a blood vessel being treated to remove blood, and administering light inside the blood vessel being treated, wherein the light is of the appropriate wavelength to activate the photosensitizer.

In specific embodiments, the methods of the present invention are practiced to inhibit the growth of or rupture of a plaque, including, e.g., a vulnerable plaque. In related embodiments, the methods of the present invention are practiced to reduce leakage of blood and/or cells from neovessels within a plaque.

In certain embodiments, the photosensitizer is administered systemically, e.g., intravenously or intraarterially, while in other embodiments, the photosensitizer is administered locally to a blood vessel to be treated.

Certain embodiments of the invention are based on the apparent isolation of the flow of blood in plaque neovascularization from the flow of blood in the lumen of the diseased artery. This creates the opportunity to distribute a photosensitizer generally in the blood through, for example, systemic intravenous injection, and then by isolating the diseased artery and flushing the blood from it, the photosensitizer will remain in the pathologic neovascularization but will be displaced from the arterial lumen where the light activation will take place. Thus, the present invention provides a highly desirable way to create a site specific treatment of pathologic neovascularization associated with atherosclerotic plaque, while mitigating collateral damage to the artery being treated by light activated treatment.

The invention also seeks to mitigate damage to the normal adventitial vasa vasorum. The use of light of appropriate wavelength as discussed above incrementally increases treatment selectivity in this regard, due to the natural attenuation of light as it passes through the tissue. The presence of the photosensitizer in the neovascularization enhances this attenuation by incrementally absorbing energy from the light, further contributing to the safety of the treatment.

The methods of the present invention may be practiced using commercially available reagents and devices, as well as those described in further detail below.

Devices and Systems for Photodynamic Therapy of Atherosclerotic Disease

This description is generally related to devices and/or systems that have one or more of the following features: a guidewire to facilitate use in the cardiovascular area; a catheter delivered using the guidewire that has a balloon or other means to gently occlude blood flow to the treatment site while allowing other devices to be placed through and beyond it to the treatment site; some means to apply a liquid flush to the vessel to flush out blood from the artery at the treatment site, for example, an injection port coupled to a flushing port; and a light emitter that emits light of a wavelength to activate the photosensitizer into the vessel wall. In particular embodiments, the catheter has a multi-channeled lumen. In one embodiment, a light treatment system for photodynamic therapy possesses all of these features.

The invention provides novel devices, apparatus, and systems that can be used, e.g., to practice the methods of the present invention. Particular embodiments of these are shown in FIGS. 3-8.

Figure 3:
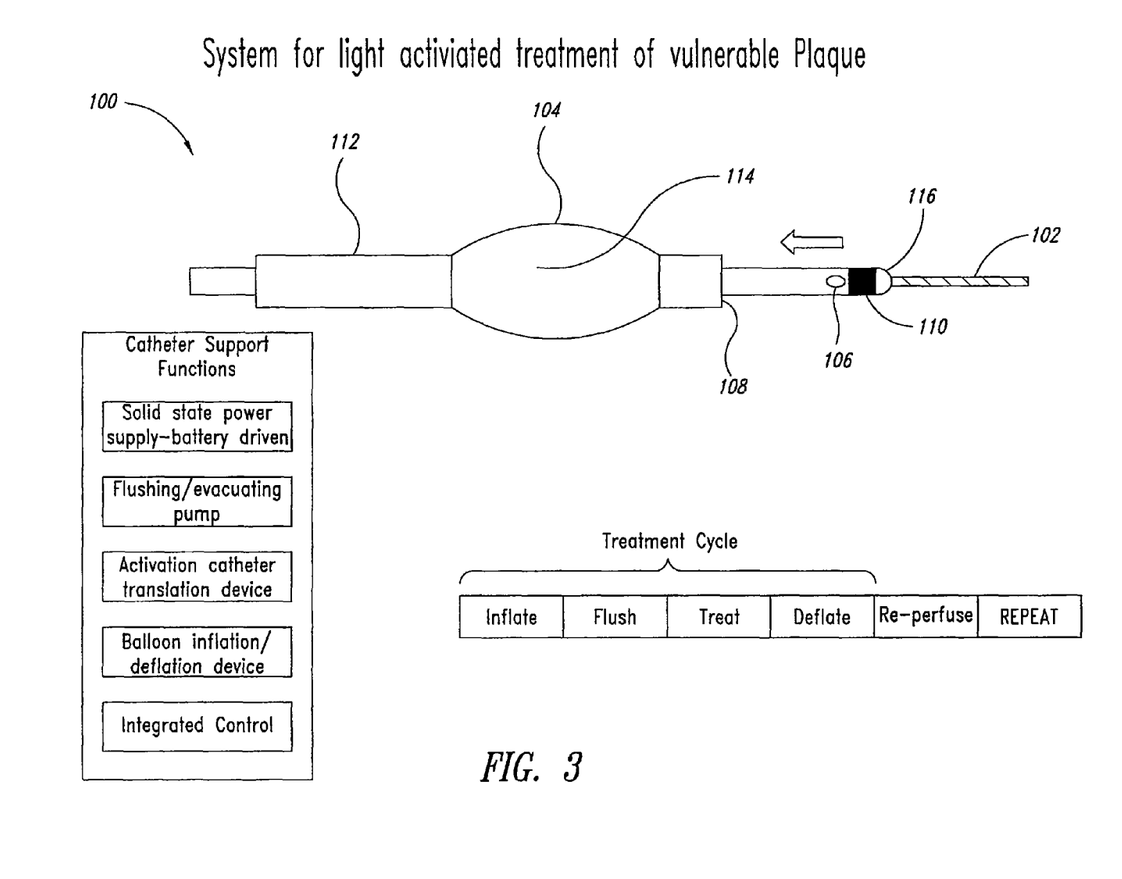
FIG. 3 is a schematic of an embodiment of a catheter of the invention that includes a balloon, a saline flushing tube, and a light source; the embodiment is shown with a guidewire inserted.

FIG. 3 illustrates an embodiment of a light treatment system 100 comprising a guidewire 102 inserted into and through a guide catheter 112 and an occlusion balloon 104. The guide catheter 112 includes a lumen for receiving the guidewire 102, means for saline flushing 106 of a blood vessel (e.g., an injection port), and light emitters 110. In the illustrated embodiment, the catheter 112 includes a passage to receive a guidewire 102 and a delivery tube for saline solution, and that is equipped with saline exit ports at or near a catheter tip 116, which may be of a soft plastic. The balloon 104 is disposed to be inflated around the catheter body and hold it in place in the vessel, when inflated. The balloon 104 may be deflated by releasing its inflation fluid (e.g., saline solution) via exit or flushing ports 108 at the proximal end of the catheter body.

In use, the catheter 112 is guided into position in the affected region of the vessel or the region desired to be treated using the guidewire 102. The arrow (FIG. 2) indicates blood flow from a distal to a proximal end of the catheter 112. The patient is treated with a dose of the photosensitizer and after sufficient time has elapsed to allow the photosensitizer to migrate to the atherosclerosis-affected field of the vessel to be treated, the balloon 104 is inflated, saline flush is applied via the injection ports 106, and the field is flushed of blood. The light emitters are then activated to deliver a dose of light. In one embodiment, light is emitted from a short emitting site in the catheter 112 and, while illuminated, is moved through the vascular region being treated at a rate of movement controlled to provide adequate energy deposition for successful light activation. In other related embodiments, the catheter is maintained in a stationary position. After a period of time depending upon patient tolerance, the emitters 110 are shut off and held stationary with respect to the vascular surface, and the balloon 104 is deflated to allow blood flow to resume and reperfuse the area. Then, the balloon 104 is re-inflated, the field is again flushed with saline, and another light dose is administered, either from the stationary light emitter 110 or from an emitter that is once again transported along the vessel. This cycle of balloon inflation, saline flushing, PDT, and balloon deflation is continued until a predetermined therapeutic light dose has been administered to treat the vessel.

In one treatment procedure, laser or non laser light emitter(s) may be used. While any light emitter of suitable size, wavelength, and power to deliver a required light dose is useful, FIGS. 4-7 show several various embodiments of light emitter configurations.

Figure 4:
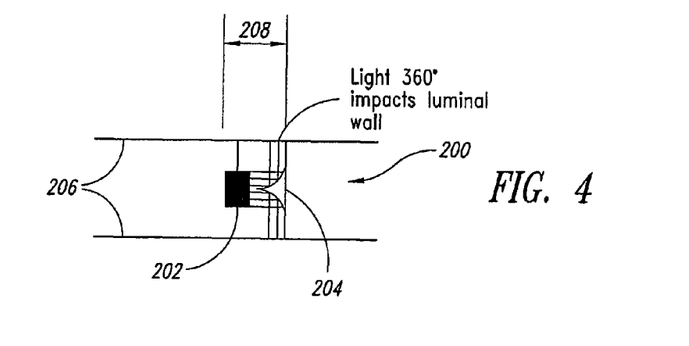

FIG. 4 shows the front end or "tip" of a light source 200 that is inserted into a blood vessel. The light is emitted from a solid state light emitter 202, such as a light emitting diode (LED) or laser emitter, and the generated light is incident upon a conical reflector 204, which reflects light radially outward, towards the wall of the vessel 206. As a result, a uniform illumination band 208 is formed around the light source. Thus the embodiment is capable of a 360-degree illumination band.

Figures 5, 6, 7:
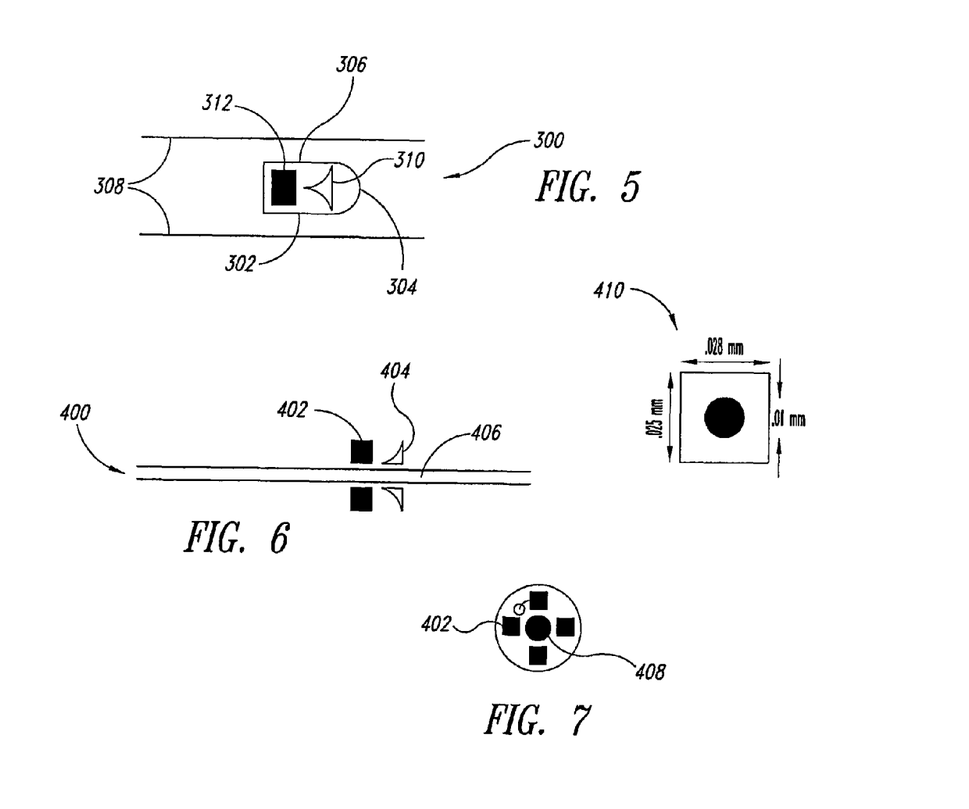

FIG. 5 shows another embodiment of the light source 300, including a lens 310 and die 312, in this instance enclosed or encased in a translucent polymer sleeve 302 that does not alter light wavelength or does so predictably. In addition, the embodiment may feature a soft polymeric tip 304 to minimize vessel trauma through contact with the vessel wall 308.

FIGS. 6 and 7 show an embodiment that has a light source, including a ring of die 402 and lens 404, and a lumen 406 sized to accommodate at least a guidewire. This embodiment, which can be used in combination with the device of FIG. 3, or any other suitable catheter, to provide the light emitters, has a plurality of emitters 410 arrayed in a circle or ring 402 around the lumen. Thus, either all or only some emitters could be activated to achieve the light pattern desired for treating a particular plaque. Insertion of the guidewire 408 provides the necessary control that physicians typically desire in the area of cardiovascular surgery.

Figure 8:
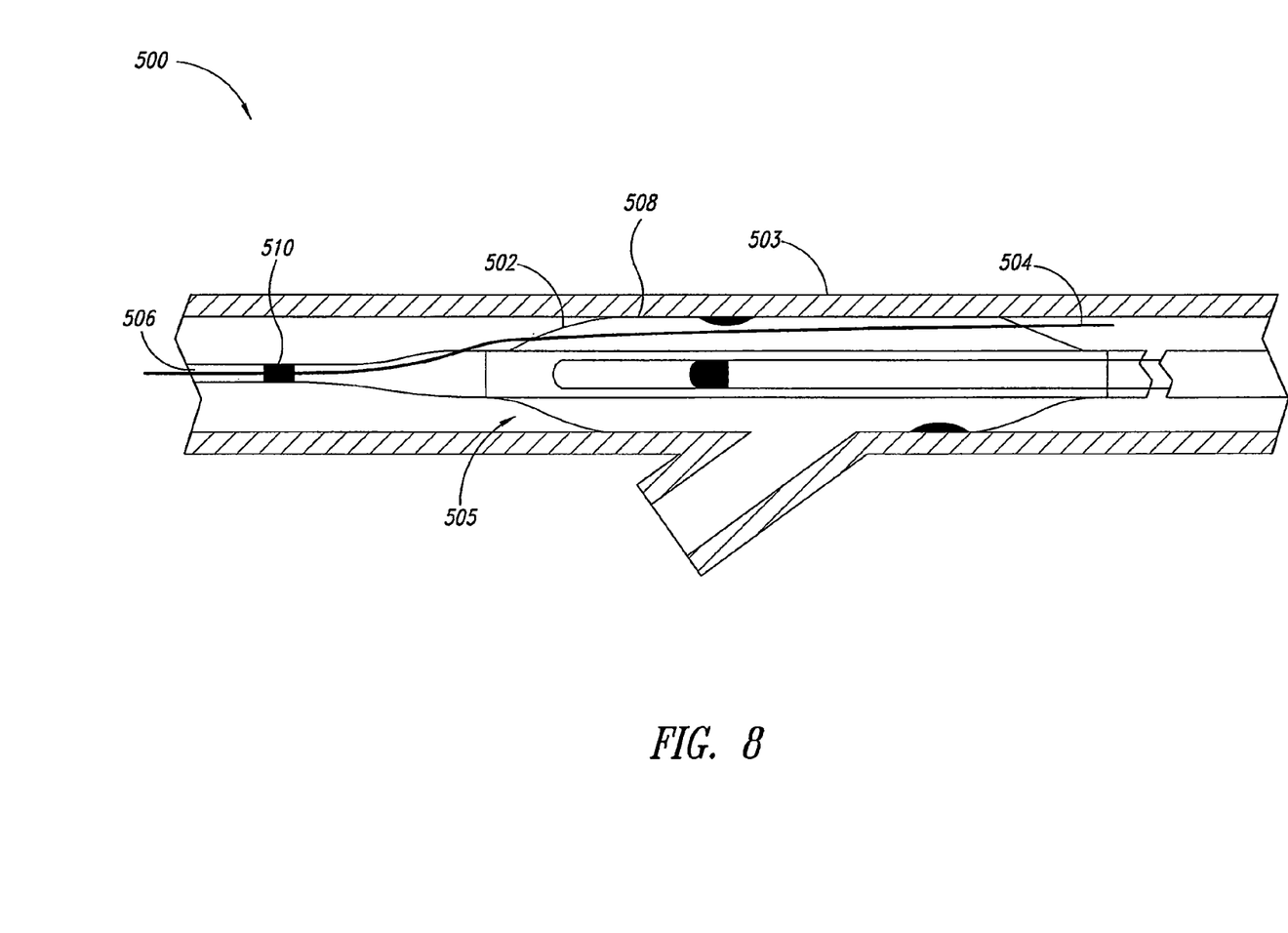
FIG. 8 is a schematic of an embodiment of a catheter of the invention that includes a balloon covering the light emitting portion.

FIG. 8 shows an embodiment of a light emitting device 500 that incorporates a balloon 502 over the entire light emitting portion 505. The balloon 502 serves to occlude the blood flow, provide a clear optical path to the vessel wall, and also provide cooling to the light emitting portion 505. The guidewire 504 is shown passing outside of the balloon 502 and through a tip 506 of the device 500. Once the device 500 is placed in the region to be treated, the balloon 502 is inflated with a low pressure, the light is activated and the emitting tip 505 is moved along the length of the balloon 502 through the central lumen. If needed, the movement can be suspended and the balloon 502 deflated to reperfuse the area. The balloon 502 would then subsequently be reinflated and treatment resumed.

Figure 9:
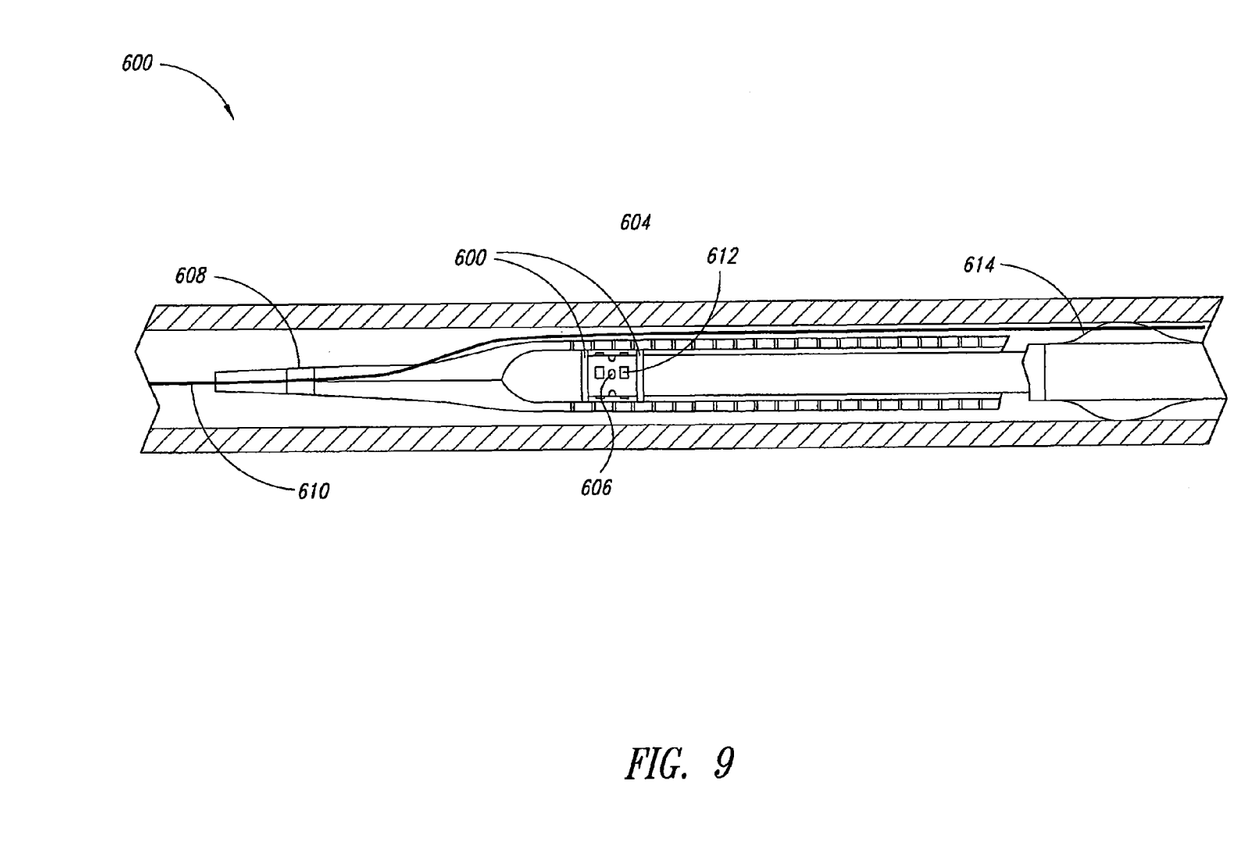
FIG. 9 is a schematic of an embodiment of a catheter of the invention that includes a moveable flushing port in close proximity to the light emitting portion.

FIG. 9 shows an embodiment that is similar to FIG. 3 but incorporates a moveable seal 602 around at least a portion of the light emitting portion 604 and a series of flushing ports 606 along the length of the device 600. The moveable seals allow a localized flushing in close proximity to the light emitting portion during treatment. This clears the blood from the treatment area in a very localized and controllable fashion and also may serve to cool the light emitting portion 604.

Figure 10:
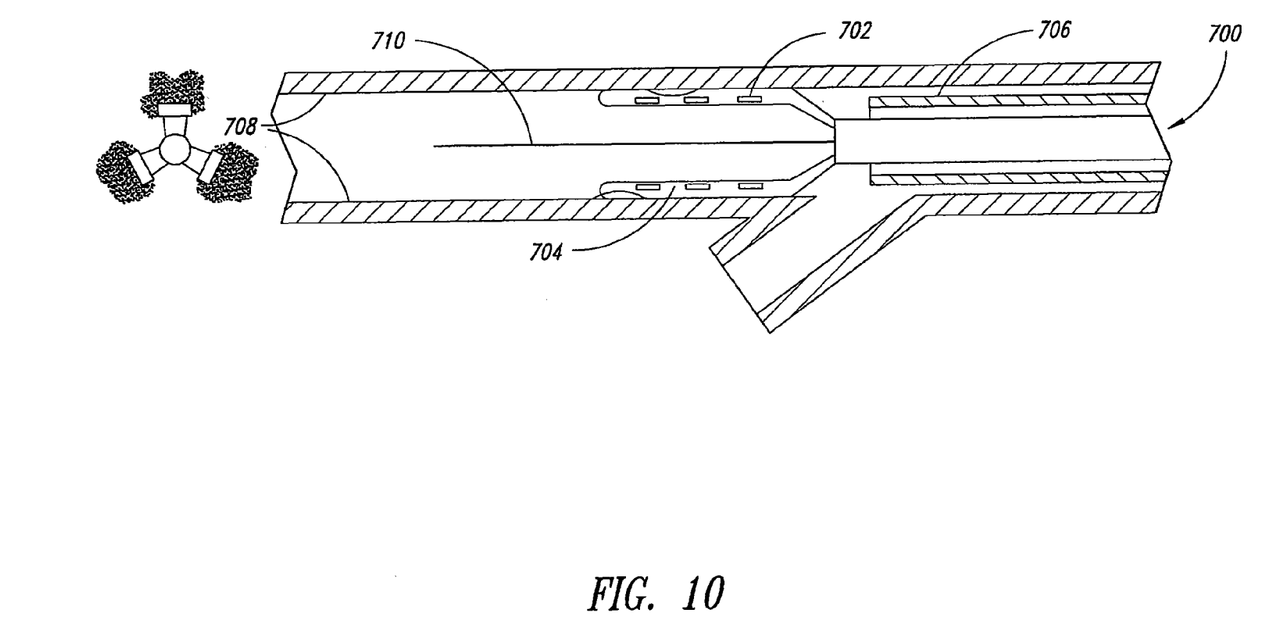
FIG. 10 is a schematic of an embodiment of a catheter of the invention that includes a deployable light emitting portion that allowing light delivery in close proximity to the vessel wall.

FIG. 10 shows an embodiment where the light emitting devices 702 are mounted on a series of flexible polymer prongs 704 laminated with a base material such a Nitinol and covered with a light diffusing material. This construction allows the device to be compressed in the catheter sheath 706 during placement to allow easy navigation to the treatment site. Prior to treatment, the sheath is withdrawn, allowing the prongs to conform to the vessel wall 708, which places the light emitters in close proximity to the treatment target. This minimizes or eliminates the need to flush or occlude the vessel because of the close proximity of the emitters to the vessel wall. The device may remain stationary during treatment and be retracted back into the sheath to remove the device.

In another embodiment, a device of the present invention comprises a catheter wherein the surface of catheter comprises one or more light emitting diodes (LEDs). In a particular embodiment, the LEDs are flexible. In one particular embodiment, two balloons are located at discrete locations of the catheter, and the LEDs are located between the two balloons. In particular embodiments, the catheter further comprises one or more ports, e.g., suitable for flushing and/or administration of a photosensitizer. In particular embodiments, the one or more ports are located between two balloons. Accordingly, the balloons may be inflated to block the vessel on either side of the balloons.

The present invention further includes systems for practicing methods of the invention, which comprise a light emitting catheter device such as one of those described above. It will be clear to those of average skill in the art that the embodiment of a catheter shown, and other catheters that perform the same functions, may require ancillary equipment such as a power supply for the light emitters and for their movement along the guidewire where that form of the invention is practiced. Within the environment where treatment with this invention will be administered, the power supply may be, for example, from disposable or re-chargeable batteries of any kind or powered by electricity. Certain embodiments of the present invention will also require a flushing and/or evacuation pump for the solutions used to flush the vessel. Further, a balloon control device for inflation and deflation may also be required for certain embodiments of the present invention. In various embodiments, systems of the present invention comprise one or more of these components, in addition to the catheter device. Preferably, but not necessarily, these are all integrated into a single mobile unit with a control panel to facilitate use in an operating room environment. Certain additional components are described in FIG. 3.

In one embodiment, a system of the present invention comprises a catheter sized for insertion into a blood vessel, the catheter comprising an inflatable balloon and a lumen; a guidewire sized to be received and extend through the lumen of the catheter; and a light source located in the lumen of the catheter to deliver light to tissue, wherein the light is delivered at an excitation wavelength that is close to an excitation wavelength of a photosensitizer. In one embodiment, the system further comprises a substance delivery system for providing a substance to the tissue, the substance delivery system including a delivery tube extending through the lumen of the catheter. The catheter may, therefore, includes a port for discharging the substance into the blood vessel. In certain embodiments, the substance is used for flushing the region of a vessel being treated, while in related embodiments, the substance is used to deliver a photosensitizer to a region of a vessel being treated. Accordingly, in particular embodiments, the substance is saline or saline in combination with an amount of a photosensitizer.

In one particular embodiment, a system of the present invention comprises a catheter sized for insertion into blood vessels to be treated with photodynamic therapy, the catheter comprising an inflatable balloon and a lumen sized to contain a guidewire; a photosensitizer having an excitation wavelength in the range from about 410 to about 475 nm; a light source sized for insertion into the lumen of the catheter to deliver light to tissue containing a concentration of the photosensitizer, the light source providing light in the excitation wavelength of the photosensitizer; and a saline flush system for delivery of flushing liquid to blood vessels to be treated, the flush system comprising a saline delivery tube sized for insertion into the lumen of the catheter. In one embodiment of a system of the present invention, the balloon of the catheter comprises fluid exit ports for deflation of the balloon, and fluid inlet ports for successive re-inflation of the balloon during stages of a photodynamic treatment procedure.

In particular embodiments of systems and methods of the present invention, the light source is a source of laser light. In additional embodiments, the photosensitizer is Talaporfin Sodium or its derivatives, or verteporfin or its derivatives, or rostaporfin or its derivatives.

The above description of illustrated embodiments, including what is described in the Abstract, is not intended to be exhaustive or to limit the invention to the precise forms disclosed. Although specific embodiments of and examples are described herein for illustrative purposes, various equivalent modifications can be made without departing from the spirit and scope of the invention, as will be recognized by those skilled in the relevant art. The teachings provided herein of the invention can be applied to various light transmission devices and/or systems, not necessarily the light transmission systems generally described above. The various embodiments described above can be combined to provide further embodiments.

All of the U.S. patents, U.S. patent application publications, U.S. patent applications, foreign patents, foreign patent applications, and non-patent publications referred to in this specification and/or listed in the Application Data Sheet, including U.S. Pat. Nos. 6,958,498; 6,784,460; 6,661,167; and 6,445,011; U.S. Publication No. 2005/0228260; International Patent Application Nos. PCT/US2005/032851 and PCT/US01/44046; U.S. patent application Ser. No. 11/323, 319, and U.S. Provisional Patent Application No. 60/640,382 are incorporated herein by reference, in their entirety. Aspects of the invention can be modified, if necessary, to employ aspects, features, and concepts of the various patents, applications, and publications to provide yet further embodiments of the invention.

These and other changes can be made to the invention in light of the above-detailed description. In general, in the following claims, the terms used should not be construed to limit the invention to the specific embodiments disclosed in the specification and the claims, but should be construed to include all light transmission systems that operated in accordance with the claims. Accordingly, the invention is not limited by the disclosure, but instead its scope is to be determined entirely by the following claims.

The invention claimed is:

1. A method of treating or preventing an acute coronary syndrome, the method comprising:
   delivering to a subject, either by systemic intravenous injection or directly into the vasculature of the subject, a dose of photosensitizer, the dose being sufficient to result in a concentration of the photosensitizer in neovascularization associated with an atherosclerotic plaque to permit effective light activated treatment;
   applying a dose of light of an appropriate wavelength to one or more regions of a vessel to excite the photosensitizer to promote closure of the neovascularization without closing a lumen of the vessel; and preventing damage to an adventitial layer of the vessel due to excitation of the photosensitizer in the adventitial layer which results in closure of blood vessels in the adventitial layer.

2. The method of claim 1, further comprising flushing blood from the one or more regions of the vessel at which the light is applied to excite the photosensitizer.

3. The method of claim 1 wherein the applying of light comprises applying light in the wavelength range from about 410 to about 475 nm.

4. The method of claim 1 wherein the photosensitizer is Talaporfin Sodium or derivatives thereof.

5. The method of claim 1 wherein the light used to excite the photosensitizer is coherent or non-coherent light.

6. The method of claim 1 wherein the application of light is to an interior surface of the vessel.

7. The method of claim 1, wherein the applying light of the appropriate wavelength further comprises applying an amount of light sufficient to excite the photosensitizer so as to promote stabilization of the atherosclerotic plaque, wherein the neovascularization associated with the atherosclerotic plaque is pathological neovascularization.

8. The method of claim 1, wherein the applying of the light comprises outputting light that interacts with the photosensitizer to reduce leakage from the neovascularization, thereby promoting stabilization of the atherosclerotic plaque, wherein the neovascularization is pathological neovascularization.

9. The method of claim 1, wherein preventing damage to the adventitial layer includes selecting the dose of light using a controller of a catheter with at least one light source for outputting the light.

10. A method of treating or preventing an acute coronary syndrome, the method comprising:
delivering to a subject, either by systemic intravenous injection or directly into the vasculature of the subject, a dose of photosensitizer, the dose being sufficient to result in a concentration of the photosensitizer in neovascularization associated with an atherosclerotic plaque to permit effective light activated treatment; and
applying light of an appropriate wavelength to one or more regions of a vessel to excite the photosensitizer to promote closure of the neovascularization, wherein the application of light to excite the photosensitizer is regionally fractionated with blood reperfusion intervals to enable a length of the vessel to be treated without occluding flow for the entire treatment process.

11. A system comprising:
a catheter sized for insertion into a blood vessel, the catheter comprising an inflatable balloon and a lumen;
a power supply;
a blue light source carried by the catheter and in electrical communication with the power supply, the blue light source is adapted to deliver blue light to the blood vessel, wherein the blue light is delivered at an excitation wavelength that corresponds to an excitation wavelength or waveband of a photosensitizer; and
a controller that controls electrical communication between the power supply and the blue light source, the controller and the power supply cooperate to deliver an amount of electrical energy to the blue light source to make the blue light source output blue light to excite a photosensitizer in regions of the vessel interior to an adventitial layer of the blood vessel to promote closure of plaque neovascularization, and the controller is configured to control the amount of electrical energy delivered to the blue light source so as to keep the blue light outputted by the blue light source from penetrating the adventitial layer and to substantially prevent damage to the adventitial layer due to closure of blood vessels in the adventitial layer.

12. The system of claim 11 further comprising a substance delivery system for providing a substance to tissue of the vessel, the substance delivery system including a delivery tube extending through the lumen of the catheter.

13. The system of claim 12, wherein the catheter includes a port for discharging the substance into the blood vessel.

14. The system of claim 11, further comprising a photosensitizer having an excitation wavelength in the range from about 410 to about 475 nm.

15. The system of claim 11 wherein the balloon of the catheter comprises fluid exit ports for deflation of the balloon, and fluid inlet ports for successive re-inflation of the balloon during stages of a photodynamic treatment procedure.

16. A system for performing therapy on a vascular vessel of a subject, comprising:
a catheter configured and sized to fit into a vascular vessel of a subject;
a power source;
a light source that receives electrical energy from the power source, the light source carried by the catheter; and
a controller in communication with the power source, the controller controls electrical energy delivered to the light source to have the light source output light to one or more regions of the vascular vessel to excite a photosensitizer present in the one or more regions of the vascular vessel to alter morphology of a wall of the vascular vessel to affect plaque neovascularization while keeping light outputted from the light source from penetrating an adventitial layer of the vascular vessel so as to prevent damage to the adventitial layer due to closure of blood vessels in the adventitial layer.

17. The system of claim 16, wherein the light source is capable of outputting light in a wavelength range from about 410 nm to about 475 nm.

18. The system of claim 16, wherein the light source is capable of outputting light that activates a dose of the photosensitizer concentrated in plaque neovascularization associated with atherosclerotic plaque.

19. The system of claim 16, wherein the light source is operable to output an amount of light that activates a therapeutically effective amount of the photosensitizer present in the one or more regions of the vascular vessel without activating a therapeutically effective amount of photosensitizer present in the adventitial layer of the vascular vessel.

20. The system of claim 16, wherein the light source is capable of promoting plaque stabilization by outputting light that interacts with the photosensitizer to reduce leakage from the neovascularization.

* * * * *